(12) United States Patent
Lipinski

(10) Patent No.: US 9,926,439 B2
(45) Date of Patent: *Mar. 27, 2018

(54) NITRILE RUBBER ARTICLE HAVING NATURAL RUBBER CHARACTERISTICS

(71) Applicant: Avent, Inc., Alpharetta, GA (US)

(72) Inventor: Timothy M. Lipinski, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 190 days.

This patent is subject to a terminal disclaimer.

(21) Appl. No.: 14/929,518

(22) Filed: Nov. 2, 2015

(65) Prior Publication Data

US 2016/0053095 A1    Feb. 25, 2016

Related U.S. Application Data

(63) Continuation of application No. 13/916,832, filed on Jun. 13, 2013, now Pat. No. 9,179,717, which is a
(Continued)

(51) Int. Cl.
*C08L 9/04* (2006.01)
*A41D 19/00* (2006.01)
(Continued)

(52) U.S. Cl.
CPC ............ *C08L 9/04* (2013.01); *A41D 19/0055* (2013.01); *A61B 42/00* (2016.02); *C08J 5/02* (2013.01); *C08L 9/02* (2013.01); *C08L 13/00* (2013.01); *A41D 2500/52* (2013.01); *C08J 2309/02* (2013.01); *C08L 2205/02* (2013.01); *C08L 2205/025* (2013.01); *Y10S 2/901* (2013.01); *Y10T 428/1352* (2015.01); *Y10T 428/266* (2015.01)

(58) Field of Classification Search
CPC .......................... B32B 27/08; Y10T 428/1352
USPC ..................... 428/35.7; 2/159, 167, 168, 901
See application file for complete search history.

(56) References Cited

U.S. PATENT DOCUMENTS

5,014,362 A   5/1991  Tillotson et al.
5,084,514 A   1/1992  Szczechura et al.
(Continued)

FOREIGN PATENT DOCUMENTS

EP    0543567 A1   5/1993
EP    1266927 A1   12/2002
(Continued)

OTHER PUBLICATIONS

American Society for Testing Materials (ASTM) Designation: D 412-98a, "Standard Test Methods for Vulcanized Rubber and Thermoplastic Elastomers-Tension," pp. 43-55, published Aug. 1998.

*Primary Examiner* — Brent T O'Hern
(74) *Attorney, Agent, or Firm* — Dority & Manning, P.A.

(57) ABSTRACT

An carboxylated nitrile-butadiene rubber latex formulation composed of a blend of a first acrylonitrile terpolymer and a second acrylonitrile terpolymer, wherein: the acrylonitrile content of the blended terpolymers is between 17 and 45% by weight, the methacrylic acid content of the blended terpolymers is less than 15% by weight, and the remaining balance of the terpolymers being butadiene. The invention also includes an elastomeric nitrile rubber article made from the formulation.

7 Claims, 4 Drawing Sheets

Related U.S. Application Data continuation of application No. 13/560,328, filed on Jul. 27, 2012, now Pat. No. 8,470,422, which is a continuation of application No. 13/370,640, filed on Feb. 10, 2012, now Pat. No. 8,250,673, which is a continuation of application No. 11/195,030, filed on Aug. 2, 2005, now Pat. No. 8,117,672.

(51) Int. Cl.
  *C08J 5/02* (2006.01)
  *C08L 9/02* (2006.01)
  *C08L 13/00* (2006.01)
  *A61B 42/00* (2016.01)

(56) References Cited

U.S. PATENT DOCUMENTS

| | | | |
|---|---|---|---|
| 5,694,326 | A | 4/1997 | Hohl et al. |
| 5,872,173 | A | 2/1999 | Anand |
| 6,000,061 | A | 12/1999 | Taneja et al. |
| 6,031,042 | A | 2/2000 | Lipinski |
| 6,391,409 | B1 | 5/2002 | Yeh et al. |
| 6,451,893 | B1 | 9/2002 | Tao |
| 6,566,435 | B1 * | 5/2003 | Teoh ............... C08L 13/02 128/844 |
| 6,624,274 | B1 | 9/2003 | Suddaby |
| 6,673,404 | B1 | 1/2004 | Yeh et al. |
| 6,673,871 | B2 | 1/2004 | Warneke et al. |
| 6,759,473 | B1 * | 7/2004 | Nakamura ............... A61L 31/10 2/161.7 |
| 6,828,387 | B2 | 12/2004 | Wang et al. |
| 7,176,260 | B2 | 2/2007 | Tao |
| 7,971,276 | B2 | 7/2011 | Eng et al. |
| 8,117,672 | B2 * | 2/2012 | Lipinski ............. A41D 19/0055 2/159 |
| 8,250,672 | B2 | 8/2012 | Lipinski et al. |
| 8,250,673 | B2 * | 8/2012 | Lipinski ............. A41D 19/0055 2/159 |
| 8,470,422 | B2 * | 6/2013 | Lipinski ............. A41D 19/0055 2/159 |
| 8,758,662 | B2 | 6/2014 | Lipinski |
| 8,835,014 | B2 | 9/2014 | Wang et al. |
| 2002/0193488 | A1 | 12/2002 | Tao |
| 2006/0235158 | A1 | 10/2006 | Ota et al. |

FOREIGN PATENT DOCUMENTS

| | | |
|---|---|---|
| EP | 1352616 A1 | 10/2003 |
| EP | 1435374 A2 | 7/2004 |
| JP | 2003268050 A | 9/2003 |
| JP | 2004131885 A | 4/2004 |
| WO | WO 97/48765 | 12/1997 |
| WO | WO 2006/124265 A1 | 11/2006 |

* cited by examiner

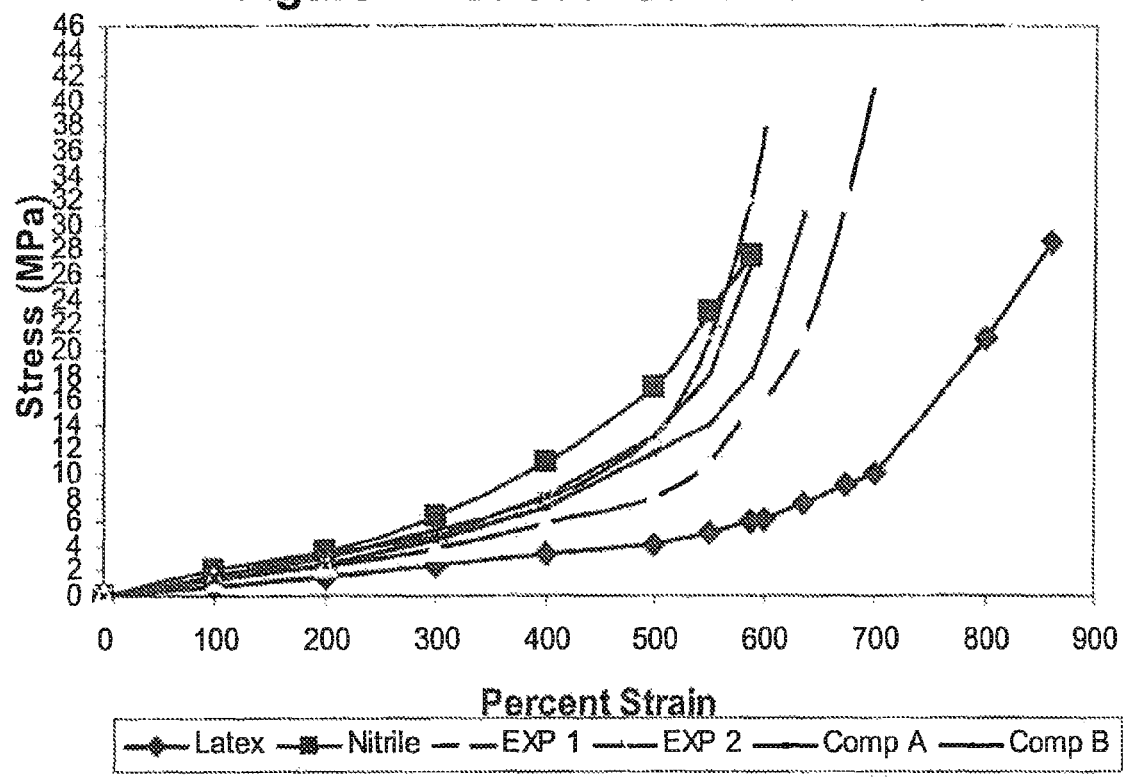

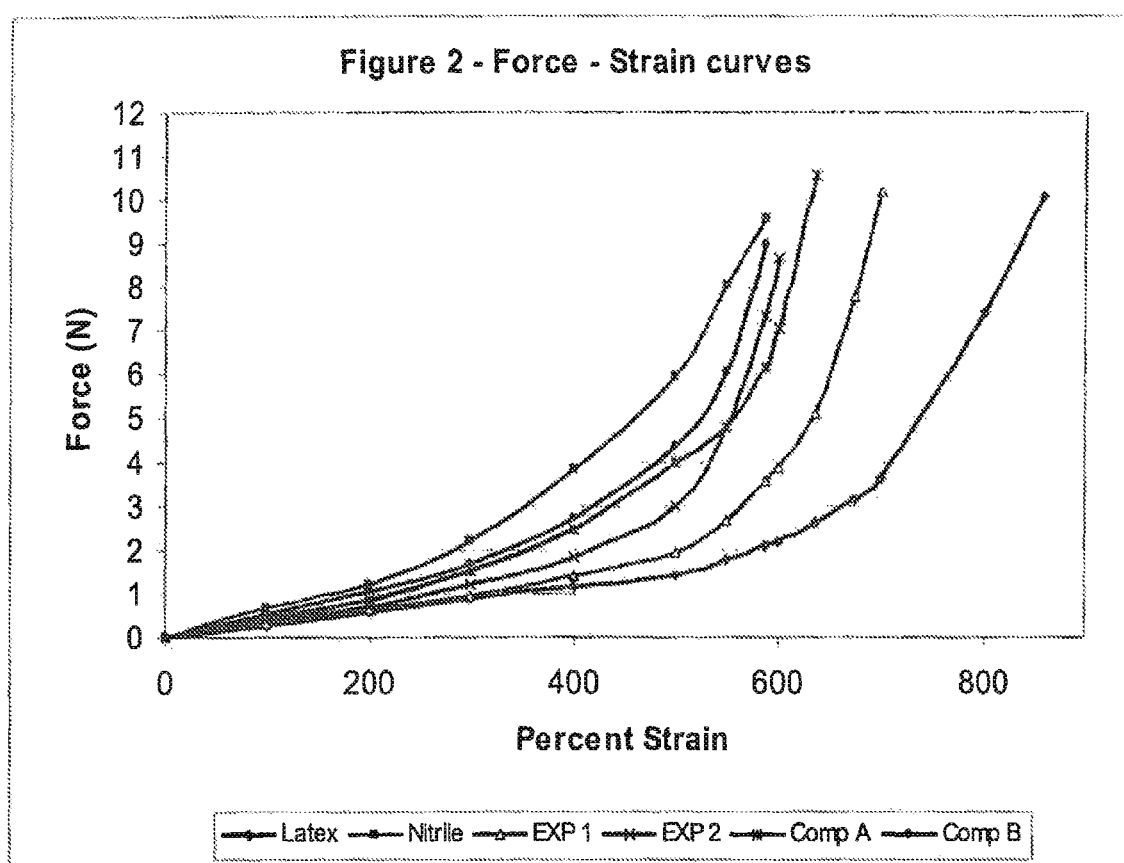

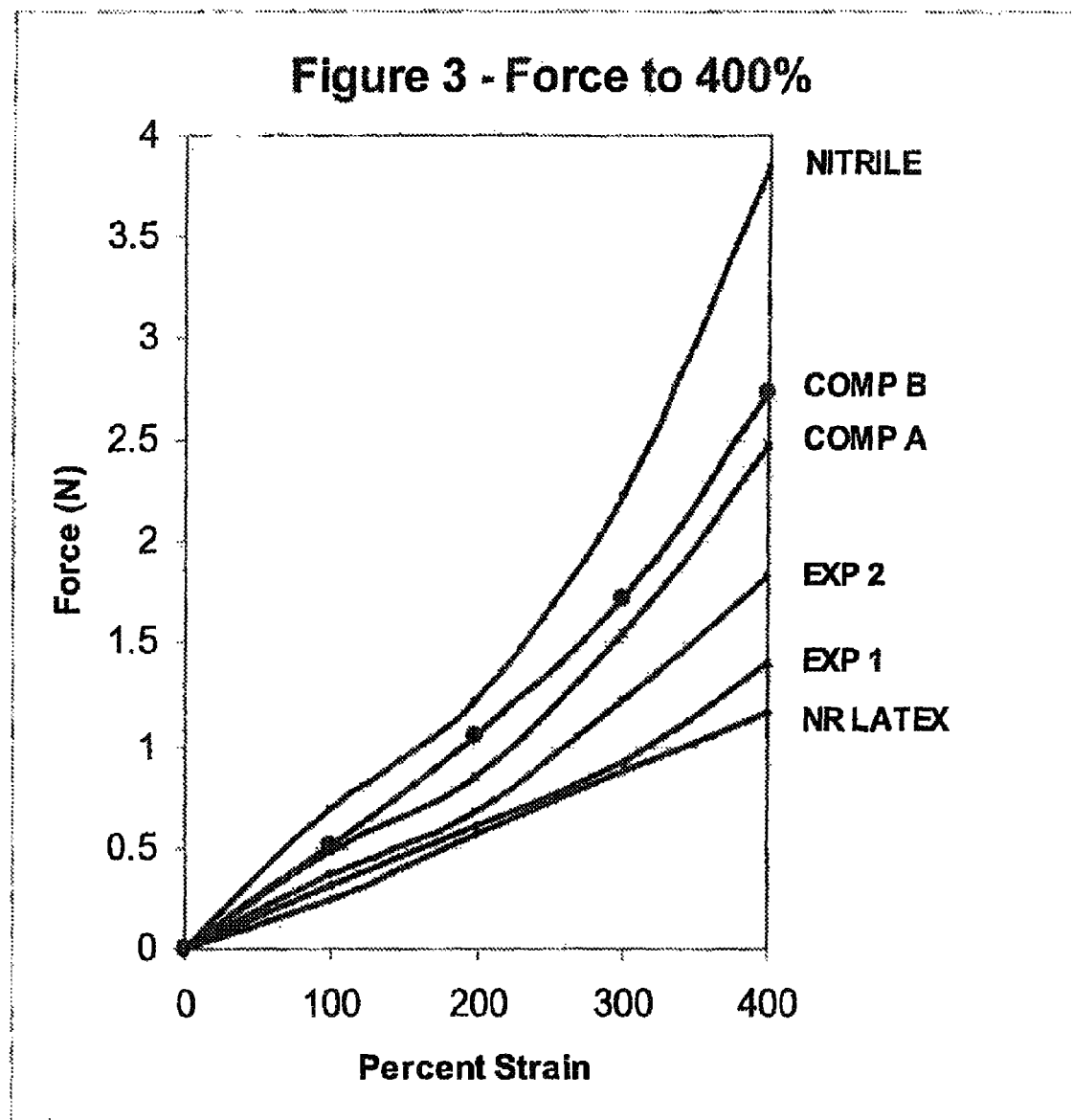

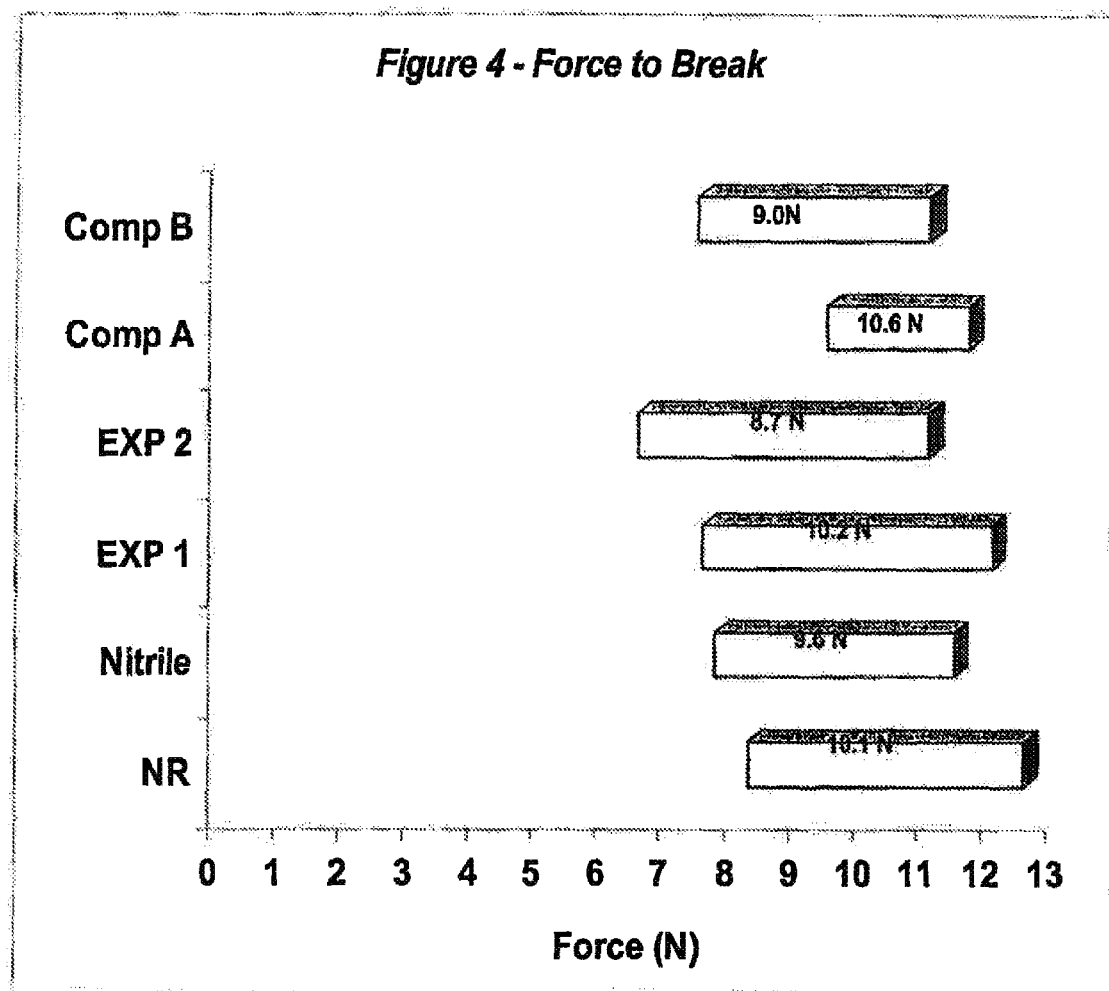

NITRILE RUBBER ARTICLE HAVING NATURAL RUBBER CHARACTERISTICS

RELATED APPLICATIONS

The present application is a divisional of U.S. patent application Ser. No. 13/916,832 "Nitrile Rubber Article Having Natural Rubber Characteristics", in the name of Timothy M. Lipinski, filed on Jun. 13, 2013 (now U.S. Pat. No. 9,179,717 issued on Nov. 10, 2015), which is a Divisional Application of U.S. patent application Ser. No. 13/560,328 "Nitrile Rubber Article Having Natural Rubber Characteristics", in the name of Timothy M. Lipinski, filed on Jul. 27, 2012 (now U.S. Pat. No. 8,470,422 issued on Jun. 25, 2013), which is a continuation of U.S. patent application Ser. No. 13/370,640 "Nitrile Rubber Article Having Natural Rubber Characteristics", in the name of Timothy M. Lipinski, filed on Feb. 10, 2012 (now U.S. Pat. No. 8,250,673 issued on Aug. 28, 2012), which is a continuation of U.S. patent application Ser. No. 11/195,030 "Nitrile Rubber Article Having Natural Rubber Characteristics", in the name of Timothy M. Lipinski, filed on Aug. 2, 2005 (now U.S. Pat. No. 8,117,672 issued on Feb. 21, 2012), and claims priority thereto.

FIELD OF THE INVENTION

The present invention relates to elastomeric articles that are made from nitrile rubber formulations. In particular, the invention pertains to carboxylated acrylonitrile butadiene rubber articles that exhibit physical characteristics that are comparable to similar articles made from natural latex rubber.

BACKGROUND OF THE INVENTION

The development of modern rubber materials has made possible the manufacture of a wide range of elastomeric articles having varying properties of strength and chemical resistance. As synthetic latex materials have developed, various elastic and polymeric materials have been adapted for use in making a variety of articles of manufacture. One useful class of synthetic rubber material compounds includes the nitrile rubber class, which is widely used to make articles such as gloves and oil resistant seals.

Elastomeric articles requiring the highest elongation and greatest ease to stretch, such as surgical or examination gloves, balloons, and condoms have traditionally been made from natural rubber latex. While nitrile rubber products are typically more difficult to stretch, one of the advantages of nitrile rubber over natural rubber latex substrates is that nitrile rubber products do not contain natural latex proteins which can become a significant allergy issue for some users. Other advantages of nitrile materials over natural rubber latex include much better chemical resistance, especially to fatty and oily substances, and better puncture resistance. Hence, nitrile-rubber-based gloves have become desirable as a substitute for natural rubber products.

While hospitals, laboratories, or other work environments that may use rubber gloves often want to go "latex free" to better protect their workers, the normally higher cost of nitrile products often limits their ability to make the change. Another hindrance toward making the change is that nitrile gloves traditionally have been stiffer, hence are much less comfortable to wear as compared to similar types of gloves made from natural rubber latex materials. For instance, natural rubber latex (NRL) examination gloves typically require a stress of about 2.5 MPa (58 psi) to stretch to an elongation of about 300% over original dimensions. This often is referred to as the glove's 300% modulus. Nitrile exam gloves, on the other hand, typically require more than twice that amount of stress (~5 MPa, 116 psi) to achieve the same 300% strain. While vinyl can be another synthetic choice, vinyl is often seen as a lower performance choice.

Currently, no synthetic latex examination gloves are available on the commercial market that exhibit force-strain properties that are close to that of natural rubber latex gloves, not to mention being either similar or the same as natural rubber-based gloves in these terms. Force-strain properties refer to a direct measurement of how a material responds (stretches) in response to an applied force, regardless of the thickness of the material. Stress-strain properties in contrast measure the response to an applied force per unit cross sectional area of the material.

Nitrile rubber, a synthetic polymer often used in emulsion (latex) form to manufacture medical and industrial gloves is a random terpolymer of acrylonitrile, butadiene, and a carboxylic acid such as methacrylic acid. It can be cross-linked by two separate mechanisms to improve its strength and chemical resistance. The first mechanism of crosslinking occurs by ionically bonding carboxylic acid groups together using multivalent metal ions. These ions are typically supplied through addition of zinc oxide to the emulsion. Normally the strength and stiffness/softness of the polymer is very sensitive to this type of crosslinking. The other crosslinking mechanism is a covalent crosslinking of the butadiene segments of the polymer using sulfur and catalysts known as rubber accelerators. This covalent crosslinking is especially important for development of chemical resistance. Gloves are often formed by first placing a coagulant solution, often calcium nitrate on ceramic glove moulds, then dipping into the nitrile latex to cause local gelation of nitrile rubber over the mould surface.

Several prior approaches to softening nitrile rubber articles involved strongly limiting or completely omitting zinc oxide and other materials capable of ionically cross-linking carboxylated nitrile rubber, such as those described in U.S. Pat. Nos. 6,031,042 and 6,451,893. In addition to not yielding force-strain properties similar to those of comparable natural rubber products, this method can result in a material having lower strength, the need for higher curing temperatures, the need for extraordinarily high levels of other chemicals that may cause skin irritation, or it may lead to processing difficulties such as thickening of the nitrile latex before dipping.

Other approaches to making a nitrile glove more comfortable, such as those described in U.S. Pat. Nos. 5,014,362 and 6,566,435, have relied on stress relaxation over time and require constantly applied levels of strain to cause that relaxation or softening. Such determination measures are difficult to maintain and can be unrealistic in real world practice and use.

A need exists for a nitrile-based polymer article that can successfully combine the benefits of nitrile materials with the greater pliability or softness of natural rubber latex without the need to apply conditions required for softening caused by stress relaxation. There is a need for a kind of nitrile glove that can incorporate a polymer formulation and product dimensions to simulate the comfort and softness associated with natural rubber latex products, while simultaneously maintaining the protective and non-allergenic properties of nitrile rubber. The glove, when worn, still enables the elastomeric material to exhibit physical strain or stress profiles similar to those of natural rubber, without exposure to natural rubber's associated problems.

SUMMARY OF THE INVENTION

The present invention pertains to an elastomeric, nitrile rubber article that exhibits the force-strain characteristics of related polyisoprene rubber articles, while preserving the tensile strength and protective properties of conventional nitrile rubber. In particular, the invention describes relatively thin elastic articles, such as glove, that is thinner and more pliable or softer than conventional nitrile gloves, but designed still to retain the protective properties and maintain sufficient strength for industrial or laboratory work and all medical procedures in which nitrile gloves are normally worn. The thinner "soft-nitrile" glove exhibits force-strain response characteristics similar to that of natural (polyisoprene) rubber gloves.

The elastic modulus of the nitrile material ranges from about 3 MPa to about 6 MPa, and the material can maintain a tensile strength in the range of about 30 or 32 MPa to about 56 or 58 MPa. While this range of modulus alone in a glove of standard thickness is not sufficient to yield natural rubber force-strain response, reducing the thickness of the article in addition to lowering its modulus meets the desired goal. While conventional nitrile examination gloves have a thickness of about 0.14±0.02 mm, the nitrile gloves according to the present invention are thinner, ranging from about 0.05 mm to about 0.10 or 0.11 mm, measured at the palm area defined by American Society for Testing and Materials (ASTM) standard D-412-98a (Reapproved 2002).

According to the present invention, by simultaneously controlling the level of crosslinking materials in the nitrile formulation and the proper article thickness, in which both kinds of controls are selected to maximize material strength and minimize the force needed to stretch the material, it is believed that one can yield a material with force response behavior similar to that of a natural latex glove of greater thickness. The crosslinking of the carboxylic acid groups is controlled by the amount and types of ionic materials added to the nitrile emulsion before it is used to produce dipped articles. The thickness of the article can be controlled by a variety of means during the dipping process.

The present approach permits one to employ more reasonable or standardized levels of chemicals and process parameters to maximize the strength potential of the nitrile rubber, while still producing a glove that is more pliable and more comfortable to wear than conventional nitrile-made articles. The present approach has advantages over the prior art. The present invention affords good flexibility in the overall levels of crosslinking agents, and gives good rate of covalent crosslinking without the need for high temperatures. It allows traditional amounts of crosslinking agents and accelerators to be used without the complications often resulting in levels of these chemicals being too high or too low. Too low a level of metal oxide, for example can result in reduced quality of the gelation process, or can cause thickening at elevated pH levels of about 8.5 and greater.

This approach does not rely on the need for stress relaxation over a period of time as long as about 10-15 minutes, nor a constant strain to effect that relaxation as others have described in previous attempts to make a more comfortable glove. The advantageous force-strain response of the present nitrile rubber-based material can be appreciated immediately by the user. The new type of nitrile-polymer can be adapted to be more pliable and comfortable to wear.

It is believed that the particular properties of the present "soft-nitrile" materials arise in part from the nature of the nitrile composition, which includes about a 50:50 blend of two acrylo-nitrile compositions. On one hand, the first nitrile composition has softer, or in other words has a lower modulus relative to the second nitrile composition. On the other hand, the second composition exhibits better film forming properties than the first composition. The properties of each composition helps to make the combined mixture for better dip processing as well as a softer more pliable material. The blend of the two compositions together achieves a synergistic effect. Such a phenomenon is a rare occurrence in the nitrile art. The orientation or placement of carboxyl groups on the nitrile polymer molecules—either outside or inside—can affect the reactivity of the carboxyl groups with cations, such as magnesium or zinc.

The present invention also details a cost effective process or means to manufacture such soft-nitrile gloves. The process entails providing a mould, applying a coagulant coating to a mould, covering at least a portion of the mould surface with nitrile compositions, such as described above, curing the nitrile composition to form a substrate, and stripping the nitrite substrate from the mould.

Additional features and advantageous of the present invention will be revealed in the following detailed description. Both the foregoing summary and the following detailed description and examples are merely representative of the invention, and are intended to provide an overview for understanding the invention as claimed.

BRIEF DESCRIPTION OF THE FIGURES

FIG. 1 is a graph showing stress-strain curves, illustrating the difference in relative amount of stretch deformation caused by a wide range of stresses applied to samples from gloves made from a natural rubber latex, three conventional nitrile formulations, and chlorinated/non-chlorinated versions of the present inventive nitrile formulation.

FIG. 2 is a graph showing the force-strain relationship for the same samples.

FIG. 3 is an enlargement of the force-strain graph in FIG. 2, showing the region between zero and four-hundred percent strain.

FIG. 4 is an illustration of the force required to break samples when tested according to ASTM D-412-98a. Ranges and averages are shown.

DETAILED DESCRIPTION OF THE INVENTION

The present invention describes the creation of elastic articles, such as gloves, made from a nitrile polymer formulation that exhibit physical characteristics similar to those of comparable natural rubber latex articles. A desirable attribute for elastomeric articles that are worn on the body is softness or pliability of the polymeric material. The invention describes the use of nitrile-based rubber formulations for manufacturing articles that have good physical strength and chemical resistance while also being softer (i.e., having a lower elastic modulus) than many previous nitrile rubber compositions. As used herein, the terms "elastic" or "elastomeric" generally refer to a material that, upon application of a force, is stretchable to an extended, biased length. Upon release of the stretching, biasing force, the material will substantially recover to near net shape or original dimensions; alternatively at least about 50% of the distorted or extended dimensions. As used herein, the term "stretch-elongation" refers to the amount or percentage that an elastomeric substrate or membrane is stretched or expanded exceeding its original dimensions. The "percentage deformation" or "percentage elongation" can be determined according to the following calculation:

Final dimension−Initial dimension/Initial dimension×100

Alternatively, the amount of elongation may be described in terms of a ratio comparing stretched length to the unstretched length. The amount of recovery (retraction upon relaxation of force), however, is a ratio based on retraction vs. stretched minus unstretched lengths. This usage is not consistent, but common. As illustration, by way of example only, an elastic material having a relaxed, unstretched length of 10 centimeters may be elongated to at least about 13.5 centimeters by the application of a stretching or biasing force. Upon release of the stretching or biasing force the elastic material will recover to a length of not more than about 12 centimeters.

Traditionally, two ways have been used to create softer, more pliable elastomeric articles. One way is to make the substrate or membrane walls of the article thinner. The second way is to reduce the elastic modulus of the elastomeric material. Each of these two approaches has associated benefits and disadvantages. For instance, in both gloves and condoms, a thinner polymer membrane tends to enable the user to experience greater tactile sensitivity. Also, often the thinner the elastic synthetic polymer walls become the less amount of force is needed to flex, stretch, or deform the article. Thinness, however, can often be associated with problems, such as weak tensile strength or tendency to rupture under use. A lower elastic or Young's modulus, on the other hand, allows one to retain a relatively thicker substrate and still impart ease of flexibility when worn on the hand. Lowering the modulus of a rubber formulation by reducing level of crosslinking in the polymer often also results in lower strength or lower chemical resistance.

The force response behavior of current nitrile gloves is normally very different from that of similar natural rubber gloves. When similar forces are applied to both kinds of materials, the amount of instantaneous stretch would be much higher for the natural rubber glove. While this difference can be reduced through various approaches, such as, most typically by reducing or even eliminating the amount of metal oxide crosslinking, reduction of the level of metal oxides to the extreme required to close the relatively large gap in difference between the two kinds of polymers often can irrevocably compromise the strength of the material body, or adversely affects the manufacturing process by dipping (i.e., slower gelation, slower covalent crosslinking, viscosity increase, etc.) while still not simulating the degree of force response associated with natural rubber very closely.

In the present invention, the extent or amount and types of ionic crosslinking can be controlled by regulating the content of all ionic materials during compounding or formulating of the nitrile latex. Rather than trying to go to an extreme high or low level of control, however, we have found a balance in the formulae that can produce sufficiently high tensile strength to lower the thickness of the dipped article, while adjusting the thickness of the material so that it requires less force to stretch than current synthetic article. By simultaneously controlling the level of crosslinkage in the material composition formula and the proper substrate thickness for the article, such that they maximize material strength and minimize the amount of force to stretch the material, one can yield a material that exhibits a force response behavior similar to that of a natural rubber latex substrate of similar or greater thickness. The crosslinking of the carboxylic acid groups is controlled by the amount and type of ionic materials added to the nitrile emulsion before it us used to produce dipped articles. The thickness of the article can be controlled by a variety of means during the dipping process, such as manipulation of the length of time that the mould form dwells in or is covered by the emulsion, temperature, or mechanical rotation or pivoting of the mould after withdraw from the dipping bath.

The gloves made using the current invention are less bulky and more pliable to wear, hence providing greater comfort compared to conventional nitrile gloves, and further can lead to cost savings in the manufacture process and ultimately to the consumer. With a thinner material, the wearer also enjoys greater tactile sensation in the hand and finger tips than compared with regular gloves. All of these advantages can be realized with no compromise in the strength of the glove.

Most nitrile rubber examination gloves that are currently available on the market have thickness of about 0.12-0.13 mm or greater. According to the present invention, we can fabricate gloves that have a lower basis weight than conventional gloves. A glove made according to the current invention has a palm thickness in a range between about 0.05 and 0.10 mm, without sacrificing the strength characteristics associated typically with thicker gloves of higher basis weight. While nitrile gloves made according to the present invention are on average 30-50% thinner than other nitrile examination gloves currently on the market, the inventive gloves are designed to still have sufficient strength to withstand industrial, laboratory, or medical procedures in which examination gloves are typically worn. A review of many nitrile examination gloves currently on the market shows the thickness in the palm area is about 0.12 mm or greater.

The precise point of measurement is that defined in American Society for Testing and Materials (ASTM) test standard D-412-98a (Reapproved 2002), "Standard Test Methods for Vulcanized Rubber and Thermoplastic Elastomers—Tension, published January 2003, the contents of which are incorporated herein by reference. These test methods cover procedures used to evaluate the tensile (tension) properties of vulcanized thermoset rubbers and thermoplastic elastomers. The determination of tensile properties start with test pieces taken from a sample material and includes the preparation of specimens and the testing of the specimens. Specimens may be in the shape of dumbbells, rings, or straight pieces of uniform cross-sectional area. Measurements of tensile stress, tensile stress at a given elongation, tensile strength, yield point, and ultimate elongation are made on specimens that have not been pre-stressed. Tensile stress, tensile strength, and yield point are based on the original cross-sectional area of a uniform cross-section of the specimen. Measurement of tensile set is make after a previously unstressed specimen has been extended and allowed to retract by a prescribed procedure.

Section I—Composition

Carboxylated nitrile, which is a terpolymer of butadiene, acrylonitrile, and organic acid monomers, has at least two properties that make it useful for manufacturing elastomeric articles. These two features are high strength and impermeability to certain hydrocarbon solvents and oils. Compounding and curing the rubber (which is used in latex form for, e.g., dipping to provide articles of manufacture such as gloves or condoms) with other ingredients such as curing agents, accelerators, and activators is generally performed to optimize these properties. The level of each monomer in the polymer and the level of curing affect the levels of strength and the chemical resistance in the finished article. Polymers with higher levels of acrylonitrile tend to have better resistance to aliphatic oils and solvents, but are also stiffer than polymers that have lower levels of acrylonitrile. While the chemical nature of the monomers from which the polymer is made offers some degree of chemical resistance, when the polymer molecules are chemically crosslinked, resistance to chemical swelling, permeation, and dissolution greatly increase.

Crosslinking also increases the strength and elasticity of the rubber. Carboxylated nitrile latexes can be chemically crosslinked in at least two ways: the butadiene subunits can be covalently crosslinked with sulfur/accelerator systems; and the carboxylated (organic acid) sites can be ionically crosslinked with metal oxides or salts. Sulfur crosslinks often result in large improvements in oil and chemical resistance. Ionic crosslinks, resulting from, for example, the addition of zinc oxide to the latex, result in a rubber having high tensile strength, puncture resistance, and abrasion resistance, as well as high elastic modulus (a measure of the force required to stretch a film of the rubber), but poor oil and chemical resistance. Many currently available rubber formulations generally employ a combination of the two curing mechanisms. For example, in combination with sulfur and accelerators, carboxylated nitrile latex manufacturers frequently recommend addition of 1-10 parts of zinc oxide per 100 parts of rubber.

While some have described ways to make softer nitrile gloves, such as detailed in U.S. Pat. Nos. 6,031,042 or 6,451,893, both of which involve formulations that contain no zinc-oxide, the present invention provides a formulation with zinc oxide, which improves the dipping qualities and cure rates. When zinc oxide is not employed, the curing time required to reach an optimum state of cure can be much longer and the curing may be less efficient. This means that the crosslinks are longer (more sulfur atoms per crosslink) and there may be a higher amount of sulfur that does not crosslink polymer chains. The result can be a less-effectively cured rubber that has lowered heat resistance and less chemical resistance. Ionic crosslinking, however, often increases the stiffness of an article made from the rubber. This is a disadvantage for applications in which a softer rubber is needed. For example, surgical gloves made of soft rubbers can provide greater tactile sensitivity for the wearer, which is desirable to improve the surgeon's "feel" during operations and to prevent fatigue of the hands.

A more comfortable nitrile glove that is easier to stretch, i.e. has lower elastic Young's modulus, can be made using a polymer which contains less acrylonitrile or by crosslinking the polymer to a lesser degree. These changes, however, often compromise strength, chemical resistance, or both, resulting in articles that are unsuitable for many applications. Accordingly, a soft rubber having strength and chemical resistance similar to stiffer rubbers is highly desirable.

The rubber membrane of the present invention is more stretchable; hence, it has been found that persons who normally need to wear a large-size glove can use a medium-size version of a glove made from the present nitrile-based composition, without binding or loss of flexible comfort. Moreover, a thinner rubber membrane enhances tactile sensitivity to temperature and surface textures.

While not intending to be bound by theory, it is believed that the matrix structure and strength of the present inventive articles may result from the interaction of all ions present in the system, in particular, divalent or higher valence cations, with the carboxylic acid components of the polymer matrix. Divalent or multivalent cations, such as Mg, Ca, Zn, Cu, Ti, Cd, Al, Fe, Co, Cr, Mn, and Pb, can crosslink with the carboxyl groups of the ionized carboxylic acids, forming relatively stable bonds. Of these cation species, Mg, Ca, Zn, Cu, or Cd are more desirable. Preferably, the methylacrylic acid monomers are located relatively close to each other in the polymer matrix structure; in such a fashion, that a divalent or multivalent cation can crosslink with two or more nearby acid units. The positive charge of the cation can well balance the negative electrons of the acidic carboxyl groups. It is believed that, absent divalent or multivalent cations, multiple polymer chains in the nitrile emulsions are not well crosslinked together. Monovalent ions, such as K, Na, or H, which do not have sufficient electron capacity to accommodate a bond with a second methylacrylic acid unit, may allow weaker forms of associative bonding. Monovalent salts that increase the pH of the system may also swell the latex particles, making more carboxylic acid groups accessible to other crosslinking agents. The positive charge of the cation can well balance the negative electrons of the acidic carboxyl groups.

In addition to slightly lowering, for example, the zinc oxide level of the formulation, it was found that addition high levels of mono-valent ions is advantageous to maintaining high strength of the material. These monovalent ions can come from alkali agents used to adjust pH of the formulation, or from other salts that do not destabilize the nitrile latex. A sulfur and rubber accelerator combination is included to provide the desired level of chemical resistance to the finished product. In some cases, a single dithiocarbamate accelerator added with sulfur is sufficient; in other cases where higher levels of chemical resistance were needed, a combination of diphenyl guanidine, zinc-mercaptobenzothiazole, and a dithiocarbamate accelerator with the sulfur provide better results.

The base polymer employed in the present nitrile material is a terpolymer composition containing acrylo-nitrile, butadiene, and carboxylic acid components. It is believed that the particular advantageous properties of the present soft nitrile materials is due in part from the nature and interaction of a blend of acrylo-nitrile components in the composition. The blend includes two—a first and a second—acrylo-nitrile formulations in a compositional ratio ranging, respectively, from about 60:40 to 40:60. The blend of the components together achieves a synergistic effect that helps to produce a softer more pliable material which also manifests better dip-processing characteristics. Such a phenomenon is a rare occurrence in the nitrile material art. The orientation or placement of carboxyl groups on the nitrile polymer molecules—either outside or inside—can affect the reactivity of the carboxyl groups with zinc ions; hence, it is believed that some components exhibit softer, lower modulus properties and some components have good film forming properties.

The acrylonitrile content of the blended or combined composition is between about 17 to 45% by weight, desirably about 20-40%, and more desirably about 20-35. Typically, the acrylonitrile content is between about 22 and 28 percent by weight, the methacrylic acid content is less than 10 percent, and the remainder of the polymer is butadiene. The methacrylic acid content should be less than about 15% by weight, preferably about 10%, with butadiene making up the remainder balance of the polymer. The base terpolymer is made through a process of emulsion polymerization, and can be used while still in emulsion form to manufacture gloves or other elastomeric articles.

The acrylonitrile polymer formulations that may be employed in the present invention can have a glass-transition temperature ($T_g$) in a range of between about −15° C. or −16° C. to about −29° C. or −30° C., under typical properties. In some embodiments, desirable nitrile polymer formulations, such as PolymerLatex X-1133 or Synthomer 6311 available from PolymerLatex GmbH, and Synthomer Ltd., respectively, have a $T_g$ between about −18° C. to about −26° C. More desirable nitrile formulations, such as Nantex 635t, commercially available from Nantex Industry Co., Ltd. (Taiwan, R.O.C.), can have a $T_g$ of about −23.4° C. to about −25.5° C. The nitrile formulation can afford higher strength than other commercially available nitrile polymers.

Reducing the thickness of the substrate membrane or skin of an elastomeric glove normally reduces its strength. To make the inventive glove thinner while still retain high strength properties, we have developed a nitrile polymer that has higher inherent strength compared to other nitrile latexes on the market. We optimize this strength advantage though our formulation and compounding methods. A relatively high pH value, in a range of about 9-12.5 or 13 is desired to optimizing the glove strength. Particular desirable pH values are about 10-11.5. The acrylonitrile polymer-containing emulsion can be adjusted to the desired pH values usually, for example, by addition of potassium hydroxide or ammonium hydroxide, at a concentration of 5 to 10%.

The nitrile emulsion is compounded, or combined with other chemicals that aid in forming the glove and give the gloves sufficient strength and durability for their intended application. Compounding of the thinner glove is done by combining the following materials. A generalized formula for this approach is as follows, with all levels listed in approximate parts per 100 parts of dry rubber:

TABLE 1

| | |
|---|---|
| Carboxylated Nitrile Latex | 100 dry parts |
| Alkali Hydroxide | 0-1.5 |
| Zinc Oxide or other Metal Oxide | 0.5-1.5 |
| Sulfur | 0.5-1.5 |
| Rubber Accelerator | 0.5-1.5 |
| Titanium Dioxide | 0-5 |
| Color Pigment | 0-1 |

Any carboxylated "nitrile," i.e. nitrile butadiene rubber, available in a latex form that may be suitable for dipping can be used. The formula can be adjusted in the ranges listed above to compensate for the varied inherent properties of the many nitrile latexes available. Some suitable examples would be Synthomer 6311 nitrile latex, manufactured by Synthomer Sdn Bhd., or Perbunan N Latex X-1133 manufactured by PolymerLatex GmbH. The titanium dioxide is used only to provide a desired level of whiteness or opaqueness.

In certain embodiments, according to the invention, a commercial nitrile latex solution as received is about 43.5% total solids content (TSC). The present nitrile emulsion compound can be prepared to have a TSC of about 15 or 16-25%. In some desirable embodiments the TSC can be about 19-22%. Depending on the strength of the coagulant, the time the glove former is allowed to dwell in the latex bath; however, this could vary and still can produce thin gloves. The finished glove has a TSC of 100%, since the substrate should not contain appreciable or significant amounts of water.

It is believed, however, that the nitrile butadiene polymer properties do not come from components of the material, but from the structure of the polymer, which in turn, is determined by polymerization conditions. Polymer properties are very much affected by the polymer structure. Molecular structure of polymers can be very complex, with variability in molecular weight, molecular weight distribution, amount of branching, amount of crosslinking during polymerization, many possible types of chemical addition for diene monomers, etc. When several monomer types are combined into a polymer such as in a carboxylated acrylonitrile butadiene polymer used for glove manufacture, the structure becomes even more complex. Overall levels of each monomer type and the sequencing of the monomer units also contribute to the properties of the resulting polymer. When the repeating structure of the monomer units are random, such as in the nitrile rubber used for gloves, the physical properties of the polymer have increased influence from the polymer linearity (vs. branching) and molecular weight as compared to the properties of a homopolymer. This is because the properties expected from a regular repeating structure of a polymer made only from each single monomer change once that repeating structure is interrupted or otherwise altered by addition of other types of monomer units. A high level of any particular monomer will likely increase the chance of contributing properties expected from a homopolymer made from that monomer, due to increased similarity of the repeating structures.

In carboxylated nitrile rubber used for thin glove manufacture, the acrylonitrile and carboxylic acid, which typically total approximately 35% add some plastic like character to the polymer with respect to resilience, permanent set, and stress relaxation. They also prevent a regular cis-1,4 repeating structure that would give polybutadiene its highest resilience and lowest set/relaxation.

A general description of such a carboxylated nitrile rubber would be a long-chain random arrangement of it's three component monomers, with branching and crosslinking. These branched, random terpolymers are former into discrete tiny particles that are emulsified in water. In addition to the polymer structure, the particle structure also plays a part in the final properties of a glove. Parameters such as particle size, particle size distribution, level of particle agglomeration, particle density, etc., affect how the product is formed, and also it's eventual properties.

In the present invention, the polymer structure includes a random terpolymer (as opposed to block or alternating terpolymer) of acrylonitrile, butadiene, and carboxylic acid. The properties depend on the average molecular weight, the molecular weight distribution, the linearity or degree of branching, the gel content (crosslinking during polymerization), and the microstructure (which monomer units are next to each other in short sections of the polymer chain.

The formulation adjustments of the present invention can lower the 300% modulus of a nitrile glove to about 3.5 MPa, but this still results in the nitrile glove requiring more force to stretch (strain) the material as compared to a natural rubber latex glove. A relatively low level of force of up to about 3.5 Newtons (N) can be used to stretch the nitrile article to about 400% original dimensions. Desirably about less than or equal to about 2.5 N.

Since the tensile strength of the gloves (i.e., stress required to break the material) from the adjusted formula is substantially higher than that of typical natural rubber gloves, reducing the glove thickness in combination with a low modulus can produce a nitrile glove with a force-strain relationship very similar to that of a NRL glove. A combination of a lower modulus cure system along with proper selection of glove thickness has yielded a nitrile elastomeric glove that has the same force-strain characteristics of natural rubber latex substrates. In other words, when an identical amount of force is applied to the present nitrile glove and a natural rubber latex glove, each gloves would exhibit a similar amount of stretchiness; hence, the two kinds of gloves would have similar comfort characteristics when worn.

Section II—Strength

While nitrile gloves made according to the present invention are on average about 30-40% thinner than gloves made from other nitrile material formulations currently available on the market, the inventive gloves are designed to still have sufficient strength to be able to withstand industrial or laboratory work, or for all medical procedures in which the gloves are normally worn. A review of many nitrile examination gloves currently on the market shows that the thickness in the palm area of the gloves is about 0.12 mm or greater. The parameters and measurement protocols are defined in *American Society for Testing and Materials* (ASTM) test standard D-412-98a. In the present invention, we employed the ASTM protocol with no changes. The testing apparatus we use is an Instron® tensometer, model 5564, with a static load cell of capacity about +/−100N, and a XL extensometer. Other similar kinds of equipments would also work, as long as the machine meets the requirements of the ASTM standard.

As stated, many nitrile examination gloves that are currently available on the market have thicknesses of about 0.12 mm or greater. According to the present invention, we can fabricate nitrile gloves that have a lower basis weight than conventional gloves. A glove according to the present invention has a palm thickness of in a range between about 0.06 and 0.10 mm, without sacrificing strength characteristics that are associated typically with thicker gloves of heavier basis-weights. "Strength" as used herein can be described as a function of the amount of force necessary to break a sample of prescribed shape and dimensions, such as those used for ASTM test standard D-412. In testing, an inventive glove with a thickness of about 0.08-0.10 mm in the palm area has an average force-at-break reading of about 8.7-10.2 newtons (N), desirably about 9.1-9.85 N, and more desirably about 9.18-9.5 N. Current market gloves have values ranging from about 6.7 to 14.3 N, with most values between 7.5 and 10.5 N.

The nitrile material of the elastic article can have a tensile strength at break in a range of about 30 MPa to about 55 MPa, desirably about 40 MPa. Typically, the amount of elongation at break would be in a range of about 550-750%, and more likely about 650%. At about 300% stretch-elongation, the modulus of the nitrile material is in a range of about 3 MPa to about 6 MPa, desirably about 4 MPa.

The level of the ionic materials is balanced in the formula to achieve the desired modulus. If the product to be made will be very thin, 0.05 mm for example, a higher modulus can be tolerated while the low thickness of the material will still result in a relatively low force required to stretch the article. In this case, the metal oxide could be used at the higher end of the stated range, together with a low to moderate level (0-0.5 phr) of alkali hydroxide or other monovalent salt. This would insure that the thinnest products would have sufficiently high tensile strength and force-to-break values.

If the desired article will be at the upper end of the thickness range discussed in association with this invention, 0.10-0.12 mm, then lower levels of metal oxide, together with moderate to high levels of alkali hydroxide (0.5-15 phr) would be chosen. Examples of these more specific formulae are:

TABLE 2

| | A | B | C | D |
|---|---|---|---|---|
| Material | | | | |
| Carboxylated Nitrile Latex | 100 | 100 | 100 | 100 |
| Ammonium Hydroxide | 0.4 | 0.0 | 0.0 | 0.78 |
| Potassium Hydroxide | 0.0 | 1.45 | 1.0 | 0.0 |
| Zinc Oxide | 1.1 | 0.25 | 0.5 | 0.25 |
| Sulfur | 1.0 | 1.0 | 1.0 | 1.0 |
| Zinc Diethyl Dithiocarbamate | 1.0 | 1.0 | 1.0 | 1.0 |
| Titanium Dioxide | 1.0 | 1.0 | 1.0 | 1.0 |
| Color Pigment | 0.2 | 0.2 | 0.2 | 0.2 |
| Resulting Properties | | | | |
| 300% Modulus (MPa) | 6.2 | 3.6 | 4.7 | 6.3 |
| Tensile Strength (MPa) | 43.1 | 35.0 | 50.0 | 50.3 |
| Force to Break at 0.05 mm thick (N) | 6.5 | 5.2 | 7.5 | 7.5 |
| Force to Break at 0.10 mm thick (N) | 13.0 | 10.4 | 15.0 | 15.0 |
| Force to 300% Strain (0.05 mm) (N) | 0.9 | 0.5 | 0.7 | 0.9 |
| Force to 300% Strain (0.10 mm) (N) | 1.8 | 1.0 | 1.4 | 1.8 |

Similar Properties for samples cut from a currently marketed natural rubber latex glove of typical thickness (0.15 mm), and a currently marketed Nitrile examination glove of thickness 0.12 mm, both manufactured by Kimberly-Clark Corporation:

TABLE 3

| | Natural Rubber | Nitrile |
|---|---|---|
| Force to Break (N): | 10.1 | 9.6 |
| Force to 300% Strain (N): | 0.8 | 2.2 |

With any of the example formulas, a thickness higher than 0.05 mm would be needed to match the force to break of Kimberly-Clark's current natural latex exam glove. While the amount of metal oxide cross linking agent in the formula may be adjusted slightly downward to achieve a lower modulus, a large adjustment is not necessarily needed nor desired since high strength resulting from these crosslinks aids in the article having sufficient strength at lowered thickness. With the force required being directly proportional to the glove thickness, the thickness required for these formulas to have a force at break of 10.1 N would be 0.078, 0.097, 0.067, and 0.067 mm respectively for example formulas A, B, C, and D. The corresponding force required to stretch these materials 300% based on these thicknesses would be 1.4, 1.0, 0.9, and 1.2 Newtons. While an examination glove made from formula C at 0.067 mm thickness would provide extremely similar properties to those of a typical natural latex examination glove, it can be seen that all of these formulas can be used to produce gloves with properties similar to those of natural rubber gloves.

It is believed that combination of a thinner material substrate thickness, the nitrile formulation used, an elevated pH≥8.5 or 9, and the procedural changes to compounding and dipping contribute to important differences between the manufacture of the present glove and the manufacture of other current nitrile examination gloves.

The accompanying figures are charts comparing gloves made 1) according to the present invention, 2) commercially available nitrile-based gloves from Kimberly-Clark Safeskin™ and 3) other comparative examples. The charts in FIGS. 1 and 2 show ranges of data for force to stretch and force to break. The present invention differs from other nitrile-based products with reference to the straight force readings that are similar to such parameters of natural rubber gloves. This phenomenon is believed to result from a combination of both modification of modulus and relative thinness of the present inventive products. Generally, the soft-nitrile articles have a much lower modulus than that of the current, competitive powder-free nitrile glove products. The synergistic effect of a reduction in thickness and retention of high tensile strength qualities is an extra feature to making the present invention unique.

FIG. 1 is a graph that compares the performance of several examples of glove membranes made from the present invention, currently available nitrile rubber based materials, and natural rubber latex. Experimental examples according to the present invention are indicated as EXP 1 and EXP 2, while comparative examples are shows as COMP A and COMP B. A standard nitrile is labeled NITRILE, and the natural rubber latex is labeled LATEX. The graph illustrates that the stresses required to strain (modulus) gloves made from the inventive formulations are reduced relative to those of current nitrile-based examination gloves. To closely simulate the stress-strain behavior of natural rubber latex examination gloves, however, the stress level of the inventive material needs to be further reduced.

FIG. 2 shows that when one reduces the relative thickness of the inventive nitrile gloves, without compromising their barrier or tensile properties, the force response (force-strain behavior) of these gloves can closely approximate or simulate that of a natural rubber glove, especially at strain levels up to about 300% or 400%, the usual range of strain that might be expected when donning and wearing an examination glove. When extended up to about 500% elongation, the examples made from the present inventive formulations can be stretched with a force of less than about 2-3 Newtons (N) to stretch, but the comparative examples require about 4 N or greater. FIG. 3 is an enlarged view of the low strain portion of the force strain chart up to 400% elongation to more clearly illustrate the advantageous feature.

The thickness of the inventive nitrile gloves were about 0.07-0.10 mm, desirably about 0.08 mm, at the palm region. The thickness of the natural rubber samples were about 0.15 mm, and the thickness of the comparative nitrile gloves from Kimberly-Clark and two other manufacturers were 0.12-0.13 mm.

To illustrate the unique properties of the present invention, data from two different soft-nitrile experimental products is included in the figures, the difference being assessment with (EXP 1) and without (EXP 2) chlorination. The non-chlorinated glove would have properties typical of a powdered glove or a polymer coated glove. Chlorination and coatings are standard methods to eliminate the need for powder on gloves. The labels NR and nitrile refer to PFE (natural rubber latex) and PFN (nitrile latex) gloves currently manufactured by Kimberly-Clark. For comparison sake, two other competitive nitrile gloves, Comparative Examples A and B are included.

FIG. 4 shows the force required to break the samples that are shown in the earlier charts. Ranges and average values are shown. As explained previously, the force required to break the samples made using the current invention can be adjusted through the level of ingredients in the formula or by adjusting the thickness of the glove. Typically, membranes made of natural rubber polymers have a failure point at about 10 N. In contrast, force at break values from various iterations of the present inventive formulation can be as high as 15 N or more, while maintaining the glove thickness less than about 0.10 mm.

Other advantages of the present invention, relative to traditional nitrile or soft-nitrile formulations include, for example, the ability to create a thinner substrate than other nitrile exam gloves, while preserving the high strength characteristics and chemical resistance comparable to that of thicker gloves. The thinness can enhance tactile sensitivity, increase comfort (thin glove with low modulus). Cost issues can also be improved for the benefit of the user. A thinner glove can help lower costs in manufacturing because of the relatively less material needed compared to thicker gloves. Additionally, for instance, one can package about 150 gloves in a standard dispenser instead of 100, for less packaging waste.

Section III—Processing

We have found that the order in which the chemicals reagents are incorporated can be significant. One can achieve improved processing and physical properties in the nitrile material from the order of addition and amounts of reagent materials. The strength of nitrile examination gloves is typically achieved by ionically crosslinking the organic acid groups contained within the polymer structure. These chemical groups can interact with a variety of cations in the system. Some cations are already in the nitrile emulsion as we receive it—counterions for the anionic surfactant used to manufacture the emulsion and cations from pH adjustment done by the manufacturer to insure stability of the product during shipment. Other cations are introduced into the system via materials that we add to the nitrile emulsion—zinc ions from zinc oxide, and potassium or ammonium ions from further pH adjustment.

Adding a base, such as either potassium or ammonium hydroxide, last in the compounding sequence increases the strength of the thin material substrate by allowing zinc from the zinc oxide to react more thoroughly with the acid groups of the nitrile polymer before the level of other cations in the system are greatly increased during the pH adjustment. This procedure also results in a glove that is easier to stretch, as measured by force readings at prescribed amounts of stretch or by modulus, which is the force per unit cross sectional area at specified levels of stretch.

Table 4, provide a summary and comparison of certain physical properties for a number of gloves samples. In particular, the properties include the force (Newtons) to stretch the elastic glove skin to about 400% original dimensions, the force (Newtons) to stretch to rupture of the glove, and the relative thickness of each sample. The physical values for a typical natural rubber latex gloves is given as a control. Examples 1-12 represent acrylo-nitrile butadiene gloves samples according to the present invention. Comparative Examples 1-8 represent typical samples of commercially-available nitrile-based gloves.

TABLE 4

| GLOVE EXAMPLE No. | FORCE (N) at 400% EXTENSION | FORCE (N) TO BREAK | THICKNESS (mm) |
| --- | --- | --- | --- |
| Natural Rubber Latex (NRL) control | 1.3 | 10.1 | 0.155 |
| Example 1 | 1.5 | 9.18 | 0.08 |

TABLE 4-continued

| GLOVE EXAMPLE No. | FORCE (N) at 400% EXTENSION | FORCE (N) TO BREAK | THICKNESS (mm) |
|---|---|---|---|
| Example 2 | 1.7 | 9.22 | 0.09 |
| Example 3 | 2.2 | 9.60 | 0.07 |
| Example 4 | 1.9 | 9.28 | 0.08 |
| Example 5 | 2.0 | 9.32 | 0.08 |
| Example 6 | 1.4 | 9.15 | 0.06 |
| Example 7 | 2.1 | 11.25 | 0.12 |
| Example 8 | 1.6 | 9.20 | 0.08 |
| Example 9 | 2.5 | 10.48 | 0.11 |
| Example 10 | 1.8 | 9.25 | 0.09 |
| Example 11 | 1.6 | 9.19 | 0.08 |
| Example 12 | 1.5 | 9.20 | 0.07 |
| Comp. Example 1 (powder free nitrile) | 6.0 | 8.2 | 0.12 |
| Comp Example 2 | 6.8 | 8.9 | 0.13 |
| Comp. Example 3 | 6.6 | 9.5 | 0.15 |
| Comp. Example 4 | 7.6 | 7.55 | 0.14 |
| Comp. Example 5 | 8.0 | 10.3 | 0.12 |
| Comp. Example 6 | 5.3 | 14.3 | 0.12 |
| Comp. Example 7 | 8.4 | 13.5 | 0.12 |
| Comp. Example 8 | 4.2 | 6.7 | 0.13 |

As one can observe, for the examples according to the present invention, one need apply only a fraction (e.g., about ½ to about ¼) of the amount of force at 400% elongation, required to achieve the same level of stretching in the eight comparative examples. This suggests that the present invention achieves a more soft and supple elastic skin, more closely resembling the stretch exhibited by natural rubber latex.

The invention is useful in manufacturing process for elastomeric articles composed of acrylonitrile materials. The invention affords, the ability to produce nitrile-based articles which closely mimics the physical properties of elastomeric articles made from natural rubber latex. The invention can be advantageously incorporated into the manufacture of a variety of products, such as medical examination or surgical gloves, condoms, probe covers, dental dams, finger cots, catheters, and the like.

The present invention has been described both in general and in detail by way of examples. Persons skilled in the art will understand that the invention is not limited necessarily to the specific embodiments disclosed. Modifications and variations may be made without departing from the scope of the invention as defined by the following claims or their equivalents, including equivalent components presently known, or to be developed, which may be used within the scope of the present invention. Hence, unless changes otherwise depart from the scope of the invention, the changes should be construed as being included herein.

A. Glove Formation

In the manufacturing of nitrile gloves, the solids content of the nitrile emulsion is reduced from 40-45% to approximately 23% in order to control the thickness of the glove. To further reduce glove thickness, solids content is reduced to approximately 20%. The thinner glove of the present invention can be fabricated by means of a coagulant dip-coating process. The process or method entails: providing a clean glove form or mould that is preheated to approximately 55-60° C., preferably about 58° C. The prepared mould is dipped into an aqueous solution of calcium nitrate. The mould, with coagulant on its surface, are dried and reheated to approximately 70° C.±5° C., and dipped into a bath of a compounded nitrile emulsion, forming a gelled glove. A beads can be rolled at the top of the glove cuff. The mould with gelled glove substrate is soaked in water to remove all of the water-soluble material components. A mould with gelled glove is dried in ovens at a temperature in the range of about 80° C. to below about 100° C. When the mould with gelled glove substrate is then heated to a higher temperature, the sulfur reacts with other chemicals and crosslinks the methylacrylic acid units in the nitrile polymer. Afterwards, the glove is removed from the mould, and the glove surfaces are treated with chlorinated water to reduce tack. Finally, the resulting gloves are dried and readied for packaging.

A faster entry and exit speeds of the glove mould into the nitrile emulsion dip can provide a more even thickness profile to the glove, and due to reduced difference in residence time of the fingertip and cuff areas of the moulds in the compounded nitrile emulsion. The mould can be extracted from the dip bath at or near an initial vertical position and raised such that the finger tips are elevated to a horizontal or greater than horizontal position (e.g, tilted to an angle about 20° to 45° above horizontal) for a brief period of a few seconds up to about 40 seconds. Quickly following, lower the finger tips to a position or angle between horizontal and initial vertical, while rolling the mould along its longitudinal axis. The raising and lowering action can be repeated in a sinusoidal or wave-like motion. This process can enable the nitrile to distribute more evenly over the former and produce a thinner overall substrate product.

Another feature for the present thinner glove is the ability to have chemical resistance equal or better than that of current, thicker, nitrile examination gloves. This could be accomplished using a combination of vulcanization accelerators. The combination includes a dithiocarbamate, a thiazole, and a guanidine compound, which, desirably, are present in the composition according to a ratio of about 1:1:2, respectively. In particular, according to an embodiment, the compounds are diphenyl guanidine (DPG), zinc mercaptobenzothizole (ZMBT), and zincdiethyldithiocarbamate (ZDEC), at about 0.5 phr DPG, 0.25 phr ZMBT, 0.25 phr ZDEC.

This combination of accelerators is very similar to that described in U.S. Pat. No. 6,828,387, incorporated herein, although the level of these chemicals is reduced by approximately 50%. This prior patent is for curing (vulcanizing) polyisoprene rubber. Unlike the '387 patent, it is believed that a double crosslinking process is involved in the present invention. In other words, relative to polyisoprene materials, crosslinking is accomplished by means of a covalent double bond in the isoprene molecule, with the present nitrile-based system, the crosslinkage is a covalent interaction with respect to the butadiene component and an ionic interaction with respect to the zinc ion and the carboxyl group of the methyl acrylic acid.

The invention is useful in manufacturing process for elastomeric articles composed of acrylonitrile materials. The invention affords, the ability to produce nitrile-based articles which closely mimics the physical properties of elastomeric articles made from natural rubber latex, without the associated latex-protein, allergenic-response issues. The invention can be advantageously incorporated into the manufacture of a variety of products, such as medical examination or surgical gloves, condoms, probe covers, dental dams, finger cots, catheters, and the like.

The present invention has been described both in general and in detail by way of examples. Persons skilled in the art will understand that the invention is not limited necessarily to the specific embodiments disclosed. Modifications and variations may be made without departing from the scope of the invention as defined by the following claims or their equivalents, including equivalent components presently known, or to be developed, which may be used within the scope of the present invention. Hence, unless changes otherwise depart from the scope of the invention, the changes should be construed as being included herein.

I claim:

1. A carboxylated nitrile-butadiene rubber latex formulation comprising a blend of a first acrylonitrile terpolymer and a second acrylonitrile terpolymer, wherein the first acrylonitrile terpolymer and the second acrylonitrile terpolymer are in a compositional ratio ranging from 60:40 to 40:60, wherein:
   the blend has an acrylonitrile content between 17 and 45% by weight, and
   the blend has a methacrylic acid content of less than 15% by weight,
   wherein a remaining balance of the blend is butadiene.

2. The formulation of claim 1, wherein the first acrylonitrile terpolymer has a lower modulus relative to the second acrylonitrile terpolymer.

3. The formulation of claim 1, wherein the carboxylated nitrile-butadiene rubber latex formulation further comprises, in terms of parts per 100 dry parts of rubber consisting of the blend of the first acrylonitrile terpolymer and the second acrylonitrile terpolymer, between 0-1.5 parts of an alkali agent that provides monovalent ions and 0.5-1.5 parts of a metallic oxide wherein a total combined amount of the alkali agent and metallic oxide is greater than 1.0 part per 100 dry parts of rubber.

4. The formulation of claim 3, further comprising in terms of parts per 100 dry parts of rubber consisting of the carboxylated nitrile-butadiene terpolymer, from 0.5-1.5 parts sulfur and 0.5-1.5 parts rubber accelerator.

5. The formulation of claim 1, wherein the formulation has a pH of 9 to 12.5.

6. The formulation of claim 1, wherein the formulation is an emulsion containing 15-25% total solids content.

7. The formulation of claim 1, wherein the formulation has a polymer structure comprising a random terpolymer of acrylonitrile, butadiene and carboxylic acid.

* * * * *